US007078483B2

(12) United States Patent
Hall et al.

(10) Patent No.: US 7,078,483 B2
(45) Date of Patent: Jul. 18, 2006

(54) RETROVIRAL VECTORS INCLUDING MODIFIED ENVELOPE ESCORT PROTEINS

(75) Inventors: Frederick L. Hall, Glendale, CA (US); Erlinda Maria Gordon, Glendale, CA (US); W. French Anderson, San Marino, CA (US)

(73) Assignee: University of Southern California, Los Angeles, CA (US)

(*) Notice: Subject to any disclaimer, the term of this patent is extended or adjusted under 35 U.S.C. 154(b) by 275 days.

(21) Appl. No.: 10/223,599

(22) Filed: Aug. 19, 2002

(65) Prior Publication Data

US 2003/0129163 A1 Jul. 10, 2003

Related U.S. Application Data

(63) Continuation of application No. 09/698,545, filed on Oct. 27, 2000, now abandoned, which is a continuation of application No. PCT/IB99/00764, filed on Apr. 28, 1999, which is a continuation-in-part of application No. 09/069,398, filed on Apr. 29, 1998, now abandoned.

(51) Int. Cl.

| | |
|---|---|
| *C07K 14/15* | (2006.01) |
| *A61K 39/12* | (2006.01) |
| *A61K 39/21* | (2006.01) |
| *C12N 15/48* | (2006.01) |

(52) U.S. Cl. ................ 530/350; 424/187.1; 424/199.1; 424/207.1; 530/395; 435/320.1

(58) Field of Classification Search ............... 435/69.1, 435/235.1, 456; 424/93.2
See application file for complete search history.

(56) References Cited

U.S. PATENT DOCUMENTS

| | | | |
|---|---|---|---|
| 5,354,674 | A | 10/1994 | Hodgson |
| 5,512,421 | A | 4/1996 | Burns et al. |
| 5,543,328 | A | 8/1996 | McClelland et al. |
| 5,591,624 | A | 1/1997 | Barber et al. |
| 5,643,770 | A | 7/1997 | Mason et al. |
| 5,681,746 | A | 10/1997 | Bodner et al. |
| 5,695,991 | A | 12/1997 | Lindholm et al. |
| 5,985,655 | A | 11/1999 | Anderson et al. |
| 6,004,798 | A | 12/1999 | Anderson et al. |

FOREIGN PATENT DOCUMENTS

| | | |
|---|---|---|
| EP | 0 334 301 A1 | 9/1989 |
| WO | WO 91/02805 | 3/1991 |
| WO | WO 92/06180 | 4/1992 |
| WO | WO 92/014829 | 9/1992 |
| WO | WO 92/20316 | 11/1992 |
| WO | WO 93/00103 | 1/1993 |
| WO | WO 93/09221 | 5/1993 |
| WO | WO 93/14188 | 7/1993 |
| WO | WO 93/25234 | 12/1993 |
| WO | WO 94/06920 | 3/1994 |
| WO | WO 94/10323 | 5/1994 |
| WO | WO 94/11524 | 5/1994 |
| WO | WO 95/23846 | 9/1995 |
| WO | WO 96/30504 | 10/1996 |
| WO | WO 97/24446 | 7/1997 |
| WO | WO 99/55893 | 11/1999 |

OTHER PUBLICATIONS

Han, X. et al., "Ligand-directed retroviral targeting of human breast cancer cells", 1995, PNAS, vol. 92: pp. 9747-9751.*
Ohno, K. et al., "Retrovirus Vectors Displaying the IgG-Binding Domain of Protein A", Oct. 1997, Biochem. and Mol. Med., vol. 62: pp. 123-127.*
Chu, Te-Hua Tearina et al., Cell Targeting WIth Retroviral Vector Particles Containing Antibody-Envelope Fusion Proteins, *Gene Therapy* (1994) 1, pp. 292-299.
Arap, et al., "Cancer Treatment by Targeted Drug Delivery to Tumor Vasculature in a Mouse Model," *Science*, 279:377-380 (Jan. 1980).
Barinaga, "Step Taken Toward Improved Vectors for Gene Transfer," *Science*, 266:1326 (Nov. 25, 1994).
Bender, et al., "Evidence that the Packaging Signal of Moloney Murine Leukemia Virus Extends into the Gag Region,"*J. Virol*, 61(5):1639-1646 (May 1987).
Cosset, et al., "Retroviral Retargeting by Envelopes Expressing an N-Terminal Binding Doman," *J. Virol.*, 69(10):6314-6322 (Oct. 1995).
Hall, et al., "Molecular Engineering Matrix-Targeted Retroviral Vectors Incorporating a Surveillance Funcint Inherent in von Willebrand Factor," *Human Geme Therapy*, 11:983-993 (May 1, 2000).
Hall, et al., "Molecular Engineering of Targeted Retroviral Vectors: Concepts, Development, and Applications," Presentation: Cold Spring Harbor Meeting, Vector Targeting Strategies for Therapeutic Gene Delivery, Mar. 11-14, 1999.

(Continued)

*Primary Examiner*—Scott D. Priebe
*Assistant Examiner*—Michael Burkhart
(74) *Attorney, Agent, or Firm*—Wilson Sonsini Goodrich & Rosati (57) ABSTRACT

A retroviral vector comprising a first retroviral envelope protein and at least one modified retroviral envelope protein, wherein the first retroviral envelope protein includes a surface protein comprising (i) a receptor binding region; (ii) a hypervariable polyproline region; and (iii) a body portion, and the modified retroviral envelope protein, prior to modification, includes a surface protein which includes (i) a receptor binding region; (ii) a hypervariable polyproline region; and (iii) a body portion, characterized in that the modified retroviral envelope protein has been modified such that at least 90% of the amino acid residues of the receptor binding region of the surface protein of the modified retroviral envelope protein have been removed and replaced with a non-retroviral protein or peptide.

2 Claims, 2 Drawing Sheets

OTHER PUBLICATIONS

Hall, et al., "Targeting Retroviral Vectors to Vascular Lesions by genetic Engineering of the MoMLV gp70 Envelope Protein," *Human Gene Therapy*, 8:2183-2192 (Dec. 10, 1997).

Han, et al., "Chimeric Envelope Glycoproteins Constructed Between Amphotropic and Xenotropic Murine Leukemia Retroviruses," *Som. Cell and Mol. Genetics*, 21(3):205-214 (1995).

Kadan, et al., "Detection of Receptor-Specific Murine Leukemia Virus Binding to Cells by Immunofluorescence Analysis," *J. Virol.*, 66(4):2281-2287 (Apr. 1992).

Kasahara, et al., "Tissue-Specific Targeting of Retroviral Vectors Through Ligand-Receptor Interactions," *Science*, 266: 1373-1376 (Nov. 25, 1994).

Martin, et al., "Retroviral Vector Targeting to Melanoma Cells by Single-Chain Antibody Incorporation in Envelope," *Human Gene Therapy*, 9:737-746 (Mar. 20, 1998).

Miller, et al., "Improved Retroviral Vectors for Gene Transfer and Expression," *Biotechniques*, 7(9):980-990 (1989).

Russell, et al., "Retroviral Vectors Displaying Functional Antibody Fragments," *Nucleic Acids Research*, 21(5): 1081-1085 (1993).

Somia, et al., "Generation of Targeted Retroviral Vectors by Using Single-Chain Variable Fragment: An Approach to in vivo Gene Delivery," *Proc. Natl. Acad. Sci. USA*, 92:7570-7574 (Aug. 1995).

* cited by examiner

Fig. 1

Fig. 2

RETROVIRAL VECTORS INCLUDING MODIFIED ENVELOPE ESCORT PROTEINS

This is a continuation of U.S. patent application Ser. No. 09/698,545, filed Oct. 27, 2000 now abandoned, which is a continuation of International Application No. PCT/IB99/00764, filed Apr. 28, 1999, which is a continuation-in-part of U.S. patent application Ser. No. 09/069,398, filed Apr. 29, 1998 now abandoned, the contents of which are incorporated herein by reference.

This invention relates to retroviral vectors which are "targeted" for binding to a desired target molecule. More particularly, this invention relates to retroviral vectors having a first envelope protein and at least one modified envelope protein. The first envelope protein includes a surface protein including a receptor binding region, a hypervariable polyproline region, and a body portion. The at least one modified envelope protein is a modified retroviral envelope protein in which at least 90% of the amino acid residues of the receptor binding region of the envelope protein are removed and replaced with a non-retroviral peptide. The non-retroviral peptide may be a ligand which binds to a desired target molecule. The term "target molecule," as used herein, means a molecule which is capable of being bound by the ligand. Such molecules include, but are not limited to, cellular receptors, extracellular components such as extracellular matrix components, and antibodies.

BACKGROUND OF THE INVENTION

Retroviral vector particles are useful agents for transducing polynucleotides into cells, such as eukaryotic cells.

Thus, retroviral vector particles have been used for introducing polynucleotides into cells for gene therapy purposes. In one approach, cells are obtained from a patient, and retroviral vector particles are used to introduce a desired polynucleotide into the cells, and such modified or engineered cells are returned to the patient for a therapeutic purpose. In another approach, retroviral vector particles may be administered to the patient in vivo, whereby the retroviral vector particles transduce cells of the patient in vivo.

In many gene therapy protocols, it would be desirable to target retroviral vector particle infection to a specific population of cells either in vivo or in vitro. In such circumstances, the broad host range of typical retroviruses present a significant problem. A key determinant of viral host range is the "envelope" or "env" protein (encoded by the env gene) which is involved in binding to receptors on the surface of susceptible cells. Where it is possible to purify the desired target cells, either before or after transduction, such purification necessitates undesirable manipulations of the cells and may be problematic in situations in which the preferred target cells either are difficult to purify or are present at low or variable frequencies in mixed cell populations. Thus, it would be advantageous to have retroviral vector particles which could infect particular types of mammalian cells.

Retroviral vectors have been made which have modified envelopes; however, such vectors in general are less infective than wild-type retroviral vectors or retroviral vectors including foreign genes, but which have unmodified envelopes.

Attempts to insert large, complex, or bulky polypeptides such as single chain antibodies, polypeptide ligands, or complement regulatory proteins have in the past been hampered by poor expression, incorporation, folding, and/or presentation of the chimeric env proteins. The present invention provides "modified env proteins" that permit the incorporation, expression and assembly of large polypeptides within the basic framework (i.e. N-terminal signal peptide, N-terminus, surface (SU) C-terminus and membrane spanning transmembrane (TM) domains) of the env protein of a virus, for example a retrovirus. These modified env proteins are devoid of much of the receptor binding domains. Hereinafter such proteins will be referred to as "escort proteins". Escort protein necessarily requires co-expression with a wild type env to gain infectivity. The "escort protein" provides the gain of function; i.e. targeting motif that directs or escorts the virus to the specific target cell or target ligand, such as IgG or exposed collagen or ECM.

A definition of the following terms is provided for the avoidance of doubt.

A "retroviral vector particle" is an infectious virion derived from a retrovirus.

A "retroviral vector plasmid vector" is a non-infectious plasmid comprising retroviral DNA, wherein said plasmid is capable of use as a vector for transfection of a target cell "Retroviral DNA" is DNA transcribed from retroviral RNA by reverse transcriptase.

SUMMARY OF THE INVENTION

It therefore is an object of the present invention to provide a retroviral vector which may be "targeted" to a desired target molecule while retaining the infectivity of wild-type retroviruses. Thus, the present invention provides a retroviral vector which includes a first envelope protein and at least one modified envelope protein. The first envelope protein includes a surface protein which includes a receptor binding region, a hypervariable polyproline region, and a body portion. Such an envelope protein may be an unmodified, or wild-type, envelope protein, or may be modified at the N-terminus without removing any portion of the receptor-binding domain, such as by insertion of a small peptide or ligand. The at least one modified envelope protein has been modified such that at least a major portion of the receptor binding region of such envelope protein has been removed and replaced with a non-retroviral protein or peptide, such as a ligand that binds to a desired target molecule.

BRIEF DESCRIPTION OF THE DRAWINGS

The invention now will be described with respect to the drawings, wherein:

FIG. 1 shows the results of an ELISA assay in which collagen-coated wells were contacted with the retroviral vectors WT-CEE, BS-CEE.CEE, BN-CEE.CEE, and BA-CEE.CEE; and FIG. 2 shows the results of an ELISA assay in which Ig G coated wells were contacted with retroviral vectors including an envelope "escort" protein which includes Protein A.

DETAILED DESCRIPTION OF THE INVENTION

In accordance with an aspect of the present invention, there is provided a modified retroviral envelope protein as will be described further hereinbelow. In general, such modified retroviral envelope, prior to modification, includes a surface protein which includes a receptor binding region, a hypervariable polyproline region, and a body portion. The modified retroviral envelope protein has been modified such that at least 90% of the amino acid residues of the receptor binding region of the surface protein have been removed and replaced with a non-retroviral protein or peptide. Such modified retroviral envelope protein in general may be included in a retroviral vector. In one embodiment, the retroviral vector includes the modified retroviral envelope protein as well as a retroviral envelope protein in which the receptor binding region, the hypervariable polyproline region, and the body portion have not been modified.

Thus, in accordance with another aspect of the present invention, there is provided a retroviral vector including a first retroviral envelope protein and at least one modified retroviral envelope protein. The first retroviral envelope protein includes a surface protein. The surface protein includes (i) a receptor binding region; (ii) a hypervariable polyproline, or "hinge" region, and (iii) a body portion. The modified retroviral envelope protein, prior to modification, includes a surface protein which includes (i) a receptor binding region; (ii) a hypervariable polyproline, or "hinge" region; and (iii) a body portion. The modified retroviral envelope protein has been modified such that at least 90% of the amino acid residues of the receptor binding region of the surface protein of the modified retroviral envelope protein have been removed and replaced with a non-retroviral protein or peptide, such as for example, a ligand which binds to a desired target molecule.

In one embodiment, at least 92% of the amino acid residues of the receptor binding region of the surface protein of the modified retroviral envelope protein have been removed and replaced with a non-retroviral protein or peptide, such as a ligand that binds to a desired target molecule. In another embodiment, all of the amino acid residues of the receptor binding region of the surface protein of the modified retroviral envelope protein have been removed and replaced with a non-retroviral protein or peptide.

In yet another embodiment, at least 90% of the amino acid residues of the receptor binding region of the surface protein of the modified retroviral envelope protein have been removed and replaced with a non-retroviral protein or peptide, and at least a portion of the amino acid residues of the hypervariable polyproline region of the surface protein of the modified retroviral envelope protein have been removed and replaced with a non-retroviral protein or peptide. In one embodiment, all of the amino acid residues of the hypervariable polyproline region of the modified retroviral envelope protein have been removed.

In a further embodiment, the receptor binding region(s) of the modified retroviral envelope protein(s), prior to modification thereof, has (have) the sequence (SEQ ID NO: 1). In the modified retroviral envelope protein(s), amino acid residues 19 through 229 of (SEQ ID NO: 1) have been removed and replaced with a non-retroviral protein or peptide. In one embodiment, amino acid residues 19 through 229 of (SEQ ID NO: 1) and at least a portion of the amino acid residues of the hypervariable polyproline region of the surface protein of the modified retroviral envelope protein(s) have been removed and replaced with a non-retroviral protein or peptide.

In general, retroviral envelope protein(s) include a surface (SU) domain, or surface protein, and a transmembrane (TM) domain or protein. In general, the surface protein includes, in an N-terminal to C-terminal direction, the following regions: (i) a receptor binding region; (ii) a hypervariable polyproline region; and (iii) a body portion, which is associated with the transmembrane domain.

The first retroviral envelope protein includes the surface domain and the transmembrane domain. In general, such envelope protein is free of non-retroviral peptides. The first retroviral envelope protein maintains wild-type infectivity. The first retroviral envelope protein, in one embodiment, may include regions of different tropisms. For example, in one embodiment, the first retroviral envelope protein may include a surface protein which includes (i) an ecotropic receptor binding region; (ii) an amphotropic hypervariable polyproline region; and (iii) an ecotropic body By "amphotropic" is meant capable of infecting both rodent and other mammalian cells including human cells. By "ecotropic" is meant capable of infecting rodent cells only.

As hereinabove stated, the modified retroviral envelope protein(s) is (are) a retroviral envelope protein(s) which is (are) modified such that at least 90% of the amino acid residues of the receptor binding region of the surface protein have been removed and replaced with a non-retroviral protein or peptide. Shown in (SEQ ID NO: 1) is the receptor binding region of the ecotropic envelope of Moloney Murine Leukemia Virus. Applicants have found that, by constructing a retroviral vector that includes a first retroviral envelope protein which maintains wild-type infectivity and retains a receptor binding region, an unmodified hypervariable polyproline region, and an unmodified body portion; and at least one modified retroviral envelope protein in which at least 90% of the amino acid residues of the receptor binding region of the surface protein have been removed and replaced with a non-retroviral protein or peptide, the modified retroviral envelope protein(s) serves as an "escort-protein" which provides one or more additional functions to the retroviral vector, such as, for example, "targeting" the retroviral vector to a desired target molecule. Such retroviral vectors, while possessing such additional functions, retain the infectivity of wild-type retroviruses.

In one embodiment, the modified retroviral envelope protein(s), prior to the modification of at least the receptor binding region to include the non-retroviral protein or peptide, may be an envelope which includes regions of different tropisms. For example, the modified retroviral envelope protein(s) may be a Moloney Murine Leukemia Virus envelope protein(s) which includes a surface protein (also known as gp 70 protein) having an ecotropic portion and an amphotropic portion and/or xenotropic portion In another embodiment, the modified retroviral envelope protein, prior to modification thereof, has a gp 70 protein which includes: (i) an ecotropic receptor binding region, i.e., (SEQ ID NO: 1); (ii) an amphotropic hypervariable polyproline region, (SEQ ID NO: 2); and (iii) an ecotropic body portion. At least 90% of the amino acid residues of the ecotropic receptor binding region (SEQ ID NO: 1) have been removed and replaced as hereinabove described, with a non-retroviral protein or peptide. In a further embodiment, at least a portion of the amphotropic hypervariable polyproline region (SEQ ID NO: 2) have been removed as well. In one embodiment, amino acid residues 1 through 35 of (SEQ ID NO: 2) have been removed. In another embodiment, amino acid residues 1 through 48 of (SEQ ID NO: 2) have been removed. In yet another embodiment, all 60 amino acid residues of (SEQ ID NO: 2) have been removed.

In a preferred embodiment, the retroviral vector particle includes a first retroviral envelope protein and a modified retroviral envelope protein. The first retroviral envelope protein includes a surface protein including a receptor binding region, a hypervariable polyproline region, and a body portion as hereinabove described. In the modified envelope protein as hereinabove described, the non-retroviral protein or peptide is a ligand which binds to a desired target molecule.

In one embodiment, the ligand includes a binding region which binds to a receptor located on a desired cell type. Such ligands include, but are not limited to, antibodies and fragments thereof, including single-chain antibodies, monoclonal antibodies, and polyclonal antibodies. Such antibodies include, but are not limited to, antibodies and fragments or portions thereof which bind to erb-B2, such as, for example, e23 antibody; antibodies which bind to receptors such as, for example, the CD4 receptor on T-cells; antibodies which bind to the transferrin receptor; antibodies directed against human leukocyte antigen (HLA); antibodies to carcinoembryonic antigen; antibodies to placental alkaline phosphatase found on testicular and ovarian cancer cells; antibodies to high molecular weight melanoma-associated antigen; antibodies to polymorphic epithelial mucin found on ovarian cancer cells; antibodies to β-human chorionic gonadotropin; antibodies to CD20 antigen of B-lymphoma cells; antibodies to alphafetoprotein; antibodies to prostate specific antigen; OKT-3 antibody, which binds to CD3 T-lymphocyte surface antigen; antibodies which bind to B-lymphocyte surface antigen; antibodies which bind to EGFR (c-erb-B1 or c-erb-B2) found on glioma cells, B-cell lymphoma cells, and breast cancer cells; anti-tac monoclonal antibody, which binds to the Interleukin-2 receptor; anti-transferrin monoclonal antibodies; monoclonal antibodies to gp 95/gp 97 found on melanoma cells; monoclonal antibodies to p-glycoproteins; monoclonal antibodies to cluster-1 antigen (N-CAM), cluster-w4, cluster-5A, or cluster-6 (LeY), all found on small cell lung carcinomas; monoclonal antibodies to placental alkaline phosphatase; monoclonal antibodies to CA-125 found on lung and ovarian carcinoma cells, monoclonal antibodies to epithelial specific antigen (ESA) found on lung and ovarian carcinoma cells; monoclonal antibodies to CD19, CD22, and CD37 found on B-cell lymphoma cells; monoclonal antibodies to the 250 kDa proteoglycan found on melanoma cells; monoclonal antibodies to p55 protein found on breast cancer cells; monoclonal antibodies to the TCR-IgH fusion protein found on childhood T-cell leukemia cells; antibodies to T-cell antigen receptors; antibodies to tumor specific antigen on B-cell lymphomas; antibodies to organ cell surface markers; anti-HIV antibodies, such as anti-HIV gp 120-specific immunoglobulin, and anti-erythrocyte antibodies.

Other ligands which may be employed include cytokines. Such cytokines include, but are not limited to, interleukins, including Interleukin-1α, Interleukin-1β, and Interleukins 2 through 14; growth factors such as epithelial growth factor (EGF), TGF-α, TGF-β, fibroblast growth factor (FGF), keratinocyte growth factor (KGF), PDGF-A, PDGF-B, PD-ECGF, IGF-I, IGF-II, and nerve growth factor (NGF), which binds to the NGF receptor of neural cells; colony stimulating factors such as GM-CSF, G-CSF, and M-CSF, leukemic inhibitory factor (LIF); interferons such as interferon-α, interferon-β, and interferon-γ; inhibin A; inhibin B; chemotactic factors; α-type intercrine cytokines; and β-type intercrine cytokines.

Still other ligands which may be employed include, but are not limited to, vascular endothelial growth factor, or VEGF, melanoma stimulating hormone, which binds to the MSH receptor on melanoma cells; the polypeptide FLA16, which has the sequence Cys-Gln-Ala-Gly-Thr-Phe-Ala-Leu-Arg-Gly-Asp-Asn-Pro-Gln-Gly-Cys, (SEQ. ID. NO. 5) which binds to the integrins VLA3, VLA4, and VLA5 found on human histiocytic lymphoma cells; the polypeptide having the structure Gly-Glu-Arg-Gly-Asp-Gly-Ser-Phe-Phe-Ala-Phe-Arg-Ser-Pro-Phe, (SEQ. ID. NO. 6) which binds to the integrin $\alpha_v\beta_3$ found on melanoma cells; erythropoietin, which binds to the erythropoietin receptor; adherins; selectins; CD34, which binds to the CD34 receptor of hematopoietic stem cells; CD33, which binds to premyeloblastic leukemia cells; stem cell factor; asialoglycoproteins, including asialoorosomucoid, asialofetuin, and alpha-1 acid glycoprotein, which binds to the asialoglycoprotein receptor of liver cells; insulin; glucagon; gastrin polypeptides, which bind to receptors on hematopoietic stem cells; C-kit ligand; tumor necrosis factors (or TNF's) such as, for example, TNF-alpha and TNF-beta; ApoB, which binds to the LDL receptor of liver cells; alpha-2-macroglobulin, which binds to the LRP receptor of liver cells; mannose-containing peptides, which bind to the mannose receptor of macrophages; sialyl-Lewis-X antigen-containing peptides, which bind to the ELAM-1 receptor of activated endothelial cells; CD40 ligand, which binds to the CD40 receptor of B-lymphocytes; ICAM-1, which binds to the LFA-1 (CD11b/CD18) receptor of lymphocytes, or to the Mac-1 (CD11a/CD18) receptor of macrophages; M-CSF, which binds to the c-fms receptor of spleen and bone marrow macrophages; VLA-4, which binds to the VCAM-1 receptor of activated endothelial cells; LFA-1, which binds to the ICAM-1 receptor of activated endothelial cells; HIV gp120 and Class II MHC antigen, which bind to the CD4 receptor of T-helper cells; and the LDL receptor binding region of the apolipoprotein E (ApoE) molecule. It is to be understood, however, that the scope of the present invention is not to be limited to any specific ligand.

In one embodiment, the ligand is a single chain antibody.

In another embodiment, the ligand includes a binding region which binds to an extracellular matrix component. The term "extracellular matrix component," as used herein, means a molecule that occupies the extracellular spaces of tissues. Such extracellular matrix components include, but are not limited to, collagen (including collagen Type I and collagen Type IV), laminin, fibronectin, elastin, glycosaminoglycans, proteoglycans, and sequences which bind to fibronectin, such as arginine-glycine-aspartic acid, or RGD, sequences. Binding regions which bind to an extracellular matrix component, and which may be included in a targeting polypeptide, include, but are not limited to, polypeptide domains which are functional domains within von Willebrand Factor or derivatives thereof, wherein such polypeptide domains bind to collagen. In one embodiment, the binding region is a polypeptide having the following structural formula: Trp-Arg-Glu-Pro-Ser-Phe-Met-Ala-Leu-Ser. (SEQ. ID. NO. 7)

Other binding regions which bind to an extracellular matrix component, and which may be included in the second retroviral envelope, include, but are not limited to, the arginine-glycine-aspartic acid, or RGD, sequences, which binds fibronectin, and a polypeptide having the sequence Gly-Gly-Trp-Ser-His-Trp, (SEQ. ID. NO. 8) which also binds to fibronectin.

In addition to the binding region, the ligand may further include linker sequences of one or more amino acid residues, placed at the N-terminal and/or C-terminal of the binding region, whereby such linkers increase rotational flexibility and/or minimize steric hindrance of the modified envelope polypeptide.

In another embodiment, the ligand is a peptide or protein which binds to an antibody. Such proteins or peptides include, but are not limited to, the Ig G-binding domain of Protein A, synthetic Ig G-binding domains, such as Protein ZZ, and Protein G.

It is to be understood, however, that the scope of the present invention is not to be limited to any specific ligand, binding region, or target molecule to which the ligand may bind.

In accordance with another aspect of the present invention, there is provided a modified polynucleotide encoding a modified retroviral envelope polypeptide (i.e., the modified retroviral envelope or "escort" protein hereinabove described). The retroviral envelope polypeptide includes a receptor binding region. In the modified polynucleotide, a polynucleotide encoding at least 90% of the amino acid residues of the receptor binding region has been removed and replaced with a polynucleotide encoding a non-retroviral protein or peptide, as hereinabove described, such as, for example, a ligand which binds to a desired target molecule.

In one embodiment, prior to modification, the polynucleotide encoding the receptor binding region encodes the sequence of (SEQ ID NO: 1). In the modified polynucleotide, a polynucleotide including the codons encoding amino acid residues 19 through 229 of (SEQ ID NO: 1) has been removed and replaced with the polynucleotide encoding the ligand. In another embodiment, a polynucleotide encoding at least a portion of the hypervariable polyproline region also has been removed as well. In one embodiment, the hypervariable polyproline region has the sequence (SEQ ID NO: 2). The receptor binding region having the sequence (SEQ ID NO: 1) is encoded by the polynucleotide having (SEQ ID NO: 3) or a degenerative derivative or analogue thereof. The hypervariable polyproline region having the sequence (SEQ ID NO: 2) is encoded by the polynucleotide having (SEQ ID NO: 4) or a degenerative derivative or analogue thereof.

The term "derivative or analogue thereof" as used herein means that the polynucleotides encoding the polypeptides (SEQ ID NO: 1) and (SEQ ID NO: 2) may have sequences different from the polynucleotides (SEQ ID NO: 3) and SEQ ID NO: 4), yet encode the same polypeptide. Such differences in polynucleotide sequences may, for example, be due to the degeneracy of the genetic code. It is also contemplated within the scope of the present invention that, prior to the modification of (SEQ ID NO: 2) or (SEQ ID NO: 4) with a polynucleotide encoding a ligand, (SEQ ID NO: 2) or (SEQ ID NO: 4) may be modified such that one or more codons encode different amino acid residues than the unmodified sequences. Such modifications may facilitate the insertion of the polynucleotide encoding the ligand.

The above polynucleotides may be constructed by genetic engineering techniques known to those skilled in the art. For example, a first expression plasmid may be constructed which includes a polynucleotide encoding the unmodified envelope protein. The plasmid then is engineered such that a polynucleotide encoding at least 90% of the amino acid residues of the receptor binding region, and which, in some embodiments, also may encode at least a portion of the hypervariable polyproline region, has been removed, whereby such polynucleotide has been replaced with a polynucleotide encoding the ligand. The polynucleotide encoding the ligand may be contained in a second expression plasmid or may exist as a naked polynucleotide sequence. The polynucleotide encoding the ligand or the plasmid containing such polynucleotide is cut at appropriate restriction enzyme sites and cloned into the first expression plasmid which also has been cut at appropriate restriction enzyme sites. The resulting expression plasmid thus includes a polynucleotide which includes the modified retroviral envelope protein. Such plasmid also includes a polynucleotide encoding a minimal signal peptide of the retroviral envelope protein. By "minimal signal peptide" is meant a signal peptide plus a cleavage site.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

In a preferred embodiment, the retroviral vector particle having a first envelope protein and a modified envelope protein in accordance with the present invention includes a polynucleotide encoding a heterologous polypeptide which is to be expressed in a desired cell. The heterologous polypeptide may, in one embodiment, be a therapeutic agent. The term "therapeutic" is used in a generic sense and includes treating agents, prophylactic agents, and replacement agents.

It is to be understood, however, that the scope of the present invention is not to be limited to any particular therapeutic agent.

The polynucleotide encoding the therapeutic agent is under the control of a suitable promoter. It is to be understood, however, that the scope of the present invention is not to be limited to specific foreign genes or promoters.

The polynucleotide encoding the therapeutic agent may be placed into an appropriate retroviral plasmid vector by genetic engineering techniques known to those skilled in the art.

In one embodiment, the retroviral plasmid vector may be derived from Moloney Murine Leukemia Virus and is of the LN series of vectors, which are described further in Bender, et al., *J. Virol.,* Vol. 61, pgs. 1639–1649 (1987) and Miller, et al., *Biotechniques,* Vol. 7, pgs 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. Pat. No. 5,672,510, which is incorporated herein by reference in its entirety.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes at least one desired polynucleotide encoding a therapeutic agent which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters for the genes contained in the vector. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

In one embodiment, the polynucleotide encoding the modified retroviral envelope protein is contained in a separate expression vehicle, such as an expression plasmid. Alternatively, the polynucleotide encoding the modified retroviral envelope protein may be contained in a retroviral plasmid vector for transduction and expression of the modified retroviral envelope protein in producer cell lines.

In one embodiment, the retroviral plasmid vector which includes a polynucleotide encoding a therapeutic agent, and the expression vehicle including the polynucleotide encoding the modified retroviral envelope protein in accordance with the invention are transduced into a packaging cell line including nucleic acid sequences encoding the gag, pol, and wild-type (i.e., unmodified) env retroviral proteins. Examples of such packaging cell lines include, but are not limited to, the PE501, PA317 (ATCC No. CRL 9078) Ψ-2, Ψ-AM, PA12, T19-14X, VT-19-17-H2, ΨCRE, ΨCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, and use of liposomes, such as hereinabove described, and $CaPO_4$ precipitation. Such producer cells generate infectious retroviral vector particles that include the first, or unmodified wild-type retroviral envelope protein, the modified retroviral envelope protein, and a polynucleotide encoding a therapeutic agent.

In another embodiment, there is provided a packaging cell which includes polynucleotides encoding the gag and pol proteins, a polynucleotide encoding a first retroviral envelope protein free of non-retroviral peptides (which in one embodiment, may be a wild-type retroviral envelope protein), and a polynucleotide encoding the modified retroviral envelope protein. A producer cell for generating retroviral vector particles which include the first and modified envelope proteins in accordance with the present invention is produced by introducing into such packaging cell either a retroviral vector particle or a retroviral plasmid vector, in each case including a polynucleotide encoding a therapeutic agent. The producer cell line thus generates infectious retroviral vector particles including the first retroviral envelope protein and the modified retroviral envelope protein and the polynucleotide encoding the therapeutic agent.

The retroviral vector particles, which include the first retroviral envelope protein and the modified retroviral envelope protein, and a polynucleotide encoding a therapeutic agent, may be administered to a host in order to express the therapeutic agent in the host. In one embodiment, the retroviral vector particles are administered to the host in an amount effective to produce a therapeutic effect in the host. The host may be a mammalian host, which may be a human or non-human primate host. In a preferred embodiment, the retroviral vector particles are administered to a host for the targeting of desired cells in vivo. The retroviral vector particles, upon administration to the host, travel to and transduce the desired target cells, whereby the transduced target cells express the therapeutic agent in vivo. When the modified retroviral envelope protein includes a ligand which binds to an antibody, the retroviral vector particles, upon administration to the host, bind to the antibody through the ligand. The retroviral vector particles and the bound antibody then travel to and transduce target cells which have a receptor which binds to the antibody. The exact dosage of retroviral vector particles which may be administered is dependent upon a variety of factors, including the age, sex, and weight of the patient, the target cells which are to be transduced, the therapeutic agent which is to be administered, and the severity of the disorder to be treated.

The retroviral vector particles may be administered systemically, such as, for example, by intravenous, intraperitoneal, intracolonic, intratracheal, endotracheal, intranasal, intravascular, intrathecal, intraarterial, intracranial, intramarrow, intravesicular, intrapleural, intradermal, subcutaneous, intramuscular, intraocular, intraosseous, and intrasynovial administration. The retroviral vector particles also may be administered topically.

Cells which may be transduced with the retroviral vector particles of the present invention include, but are not limited to, primary cells, such as primary nucleated blood cells, primary tumor cells, endothelial cells, epithelial cells, vascular cells, keratinocytes, stem cells, hepatocytes, chondrocytes, connective tissue cells, fibroblasts and fibroelastic cells of connective tissues, mesenchymal cells, mesothelial cells, and parenchymal cells; smooth muscle cells of the vasculature; hematopoietic stem cells; T-lymphocytes; B-lymphocytes; neutrophils; macrophages; platelets; erythrocytes; reparative mononuclear granulocytic infiltrates of inflamed tissues; nerve cells; brain cells; muscle cells; osteocytes and osteoblasts in bone; lung cells, pancreatic cells; epithelial and subepithelial cells of the gastrointestinal and respiratory tracts; and malignant and non-malignant tumor cells. The selection of the particular cells which are to be transduced is dependent upon the disease or disorder to be treated as well as the ligand contained in the second retroviral envelope protein. It is to be understood that the scope of the present invention is not to be limited to the transduction of any specific target cells.

Diseases or disorders which may be treated with the retroviral vector particles of the present invention include, but are not limited to, severe combined immune deficiency caused by adenosine deaminase deficiency; sickle cell anemia; thalassemia; hemophilia A and B; diabetes; emphysema caused by α-1-antitrypsin deficiency; Alzheimer's disease; AIDS; chronic granulomatosis; Gaucher's disease; Lesch-Nyhan syndrome; muscular dystrophy, including Duchenne muscular dystrophy; Parkinson's disease; cystic fibrosis; phenylketonuria; hypercholesterolemia; and other illnesses such as growth disorders and heart diseases, such as, for example, those caused by alterations in the way cholesterol is metabolized and defects in the immune system, and other cardiovascular diseases.

When the modified retroviral envelope protein of the retroviral vector particle includes a ligand which binds to an extracellular matrix component, such retroviral vector particles may be employed in treating diseases or disorders which are associated with an exposed extracellular matrix component. Such diseases or disorders include, but are not limited to, cardiovascular diseases; cirrhosis of the liver; and connective tissue disorders (including those associated with ligaments, tendons, and cartilage), and vascular disorders associated with the exposition of collagen. The retroviral vector particles may be used to deliver therapeutic genes to restore endothelial cell function and to combat thrombosis, in addition to limiting the proliferative and fibrotic responses associated with neointima formation. The retroviral vector particles also may be employed in treating vascular lesions; ulcerative lesions; areas of inflammation; sites of laser injury, such as the eye, for example; sites of surgery; arthritic joints; scars; and keloids. The retroviral vector particles also may be employed in wound healing.

In addition, retroviral vector particles which include the modified retroviral envelope protein hereinabove described wherein said modified retroviral envelope protein includes a ligand which binds to an extracellular matrix component also may be employed in the treatment of tumors, including malignant and non-malignant tumors. Although Applicants do not intend to be limited to any theoretical reasoning, tumors, when invading normal tissues or organs, secrete enzymes such as collagenases or metalloproteinases which provide for the exposition of extracellular matrix components. By targeting retroviral vector particles to such exposed extracellular matrix components, the retroviral vector particles become concentrated at the exposed matrix components which are adjacent the tumor, whereby the retroviral vector particles then infect the tumor cells. Such tumors include, but are not limited to, carcinomas; sarcomas, including chondrosarcoma, osteosarcoma, and fibrosarcoma; and brain tumors. For example, a retroviral vector particle, including the modified retroviral envelope protein as hereinabove described and which includes a ligand which binds to an extracellular matrix component located at a tumor site, and a polynucleotide encoding a negative selective marker or "suicide" gene, such as, for example, the Herpes Simplex Virus thymidine kinase (TK) gene, may be administered to a patient, whereby the retroviral vector particles transduce the tumor cells. After the tumor cells are transduced with the retroviral vector particles, an interaction agent or prodrug, such as gancyclovir or acyclovir, is administered to the patient, whereby the transduced tumor cells are killed.

It is to be understood that the present invention is not to be limited to the treatment of any particular disease or disorder.

The retroviral vector particles, which include the first retroviral envelope protein and the modified retroviral envelope protein hereinabove described and a polynucleotide encoding a therapeutic agent, may be administered to an animal in vivo as part of an animal model for the study of the effectiveness of a gene therapy treatment. The retroviral vector particles may be administered in varying doses to different animals of the same species, whereby the retroviral vector particles will transduce the desired target cells in the animal. The animals then are evaluated for the expression of the desired therapeutic agent in vivo in the animal. From the data obtained from such evaluations, one may determine the amount of retroviral vector particles to be administered to a human patient.

The retroviral vector particles of the present invention also may be employed in the in vitro transduction of desired target cells, which are contained in a cell culture containing a mixture of cells. Upon transduction of the target cells in vitro, the target cells produce the therapeutic agent or protein in vitro. The therapeutic agent or protein then may be obtained from the cell culture by means known to those skilled in the art.

The retroviral vector particles also may be employed for the transduction of cells in vitro in order to study the mechanism of the genetic engineering of cells in vitro.

In addition, the "escort-protein" which forms the modified retroviral envelope protein may be employed to form proteoliposomes; i.e., the "escort-protein" forms a portion of the liposome wall. Such proteoliposomes may be employed for gene transfer or for drug delivery to desired target cells.

In another embodiment, the retroviral vector particles may include, in addition to the first retroviral envelope protein and the modified retroviral envelope protein hereinabove described, one or more additional modified envelope proteins, wherein the non-retroviral protein(s) or peptide(s) which replaces the amino acid residues which were removed from the unmodified envelope protein provides an additional function(s) to the retroviral vector particles. Such functions include, but are not limited to, complement regulation or complement resistance, resistance to humoral and cellular immune responses, and stimulation of the growth of cells to which the retroviral vector particle may be targeted, thereby enabling more target cells to be infected by the retroviral vector particle. Examples of such proteins or peptides which may be placed in the additional retroviral envelope protein(s) include, but are not limited to, complement regulatory proteins or complement resistance proteins such as CD55, CD46, and CD59; immunosuppressive agents such as TGF-β1 and Interleukin-10; and growth factors and cytokines including, but not limited to, EGF, IGF, VEGF, and all interleukins. Such additional modified envelope proteins may be generated by transducing a polynucleotide encoding such a modified envelope protein into a packaging cell as hereinabove described. Thus, one may construct a retroviral vector particle that may be targeted to a particular cell, and possess additional properties such as those hereinabove described.

In one preferred embodiment, the retroviral vector particle has, in addition to the first retroviral envelope protein, first and second modified retroviral envelope proteins as hereinabove described. In the first modified retroviral envelope protein, the non-retroviral protein or peptide is a ligand which binds to a desired target molecule. In the second modified retroviral envelope protein, the non-retroviral protein or peptide is a complement regulatory protein. Such a retroviral vector particle may be administered to a host, whereby the retroviral particle is targeted to a desired cell, retains the infectivity of wild-type retrovirus, and is resistant to complement.

EXAMPLES

The invention now will be described with respect to the following examples; however, the scope of the present invention is not intended to be limited thereby.

Example 1

Construction of Retroviral Vectors Having an Escort Protein Which Binds to Collagen Synthetic oligonucleotides encoding a collagen binding domain with strategic linkers were generated. The polypeptide including the collagen binding domain and linkers has the following sequence:

GHMWREPSFMALSGAS (SEQ ID NO:9).

The following synthetic oligonucleotides encoding the above polypeptide also were synthesized by the USC Microchemical Core Facility as deoxyoligonucleotides.

```
                                    (SEQ ID NO:10)
Sense:     5'-TAACCGGCCATATGTGGCGCGAA
              BstEII
              CCGAGCTTCATGCTCTGAGCGGTGCTAGCAAC-3'.

(SEQ ID NO:11)
Antisense: 3'-GCCGGTATACACCGCGCTTGGCTCGA
              AGTACGAGACTCGCCACGATCGTTGGATC-5'.
                                            AvrII (SEQ ID NO:12)
Sense:     5'-GTAACCGGCCATATGTGGCGCGAACC
              BstEII
              GAGCTTCATGGCTCTGAGCGGTGCTAGCG -3'.

(SEQ ID NO:13)
Antisense: 3'-GCCGGTATACACCGCGCTTGGCTCGA
              AAGTACCGAGACTCGCCACGATCGCGGCC-5'.
                                          NgoMI (SEQ ID NO:14)
Sense:     5'-GTAAC CGGCCATATGTGGCGCGAA
              BstEII
              CCGAGCTTCATGGCTCTGAGCGGTGCTAGCTCAGG-3'.
                                                 StuI (SEQ ID.NO:15)
Antisense: 3'-GCCGGTATACACCGCGCTTGGCTCG
              AAGTACCGAGACTCGCCACGATCGAGTCC-5'.
                                         StuI
```

The tandem synthetic oligonucleotides were heated to 95° C. and allowed to anneal by gradual cooling to room temperature. The DNA duplexes were separated from single-stranded oligonucleotides by passage through a G25 column (5 Prime® 3 Prime, Inc., Boulder, Colo.). Agarose gels were used to confirm the purity and conformation of the synthetic oligonucleotide inserts.

The inserts were cloned into the CEE (ecotropic)—delta hinge env construct (Wu, et al., *J. Virol.*, July 1998, p 5383–5391), which was modified by replacement of an amphotropic hypervariable polyproline or "hinge" region (SEQ ID NO: 2) containing three unique restriction sites (AvrII (at codon 1 of the "hinge" region), PstI (at codon 35 of the "hinge" region), StuI (at codon 48 of the "hinge" region)), and an NgoMI restriction site (at codon 60 of the "hinge" region). The vector was cut with the following restriction enzymes to generate the respective constructs: BstEII insert; BstEII to AvrII; BstEII to PstI; BstEII to StuI; BstEII to NgoMI; and StuI insert. The linearized vectors were confirmed by restriction analysis on agarose gels and purified by the GeneClean method (Bio 101, Vista, Calif.), prior to ligation with the respective collagen binding domain inserts and T4 DNA ligase (New England Biolabs, Beverly, Mass.) for either 3 hours at room temperature or overnight at 4° C.

After ligation, the various constructs of plasmid DNA were transformed into XL1 Blue strain of *E. coli* and grown on LB agar plates under ampicillin selection. Plasmid DNA was extracted from selected transformed clones using QIA prep Miniprep Kits (Qiagen, Valencia, Calif.). Each construct was confirmed by digestion with the appropriate restriction enzymes described above and analysis of the respective inserts. Restriction analysis was followed by direct DNA sequence analysis using the T7 Sequenase sequencing kit (Amersham Life Science, Inc., Cleveland, Ohio).

The plasmids containing the coding sequences for the modified envelope proteins, which include the 18 amino acid residues of the N-terminal of the receptor binding region of the ecotropic envelope, the collagen binding domain, a portion of the hypervariable polyproline region of amphotropic envelope protein, the remaining C-terminus of the surface protein, and the transmembrane proteins, sometimes are hereinafter referred to as "pESCORT."

Retroviral vectors bearing "escort" protein constructs were assembled using a four-plasmid transient transfection system modified from Soneoka, et al., *Nucleic Acids Research,* Vol. 23, pgs. 628–633 (1995), in which the wild-type (amphotropic or ecotropic) envelope was co-expressed. The four plasmids employed were (i) pHIT 112; (ii) pHIT60; (iii) one of the pESCORT plasmids; and (iv) either pCAE or pCEE (Morgan, et al., *J. Virol.,* Vol. 67, No. 8, pgs. 4712–4721 (August 1993)). Plasmid pHIT60, provided by Dr. Paula Cannon, University of Oxford, Oxford, United Kingdom, includes the SV40 origin of replication and the retroviral gag-pol gene under the control of a cytomegalovirus (CMV) promoter. Plasmid pHIT112, provided by Ling Li, USC Gene Therapy Laboratories, Los Angeles, Calif., includes a LacZ gene under the control of a hybrid CMV-LTR promoter, and a neomycin resistance gene under the control of the SV40 promoter. 10 mg of each plasmid were cotransfected by the calcium phosphate method into 293 T cells, which express SV40 large T antigen. (Pear, et al., *Proc. Nat. Acad. Sci.,* Vol. 90, pgs. 8392–8396 (September 1993)). The producer cells were treated subsequently with 10 mM sodium butyrate for 8 to 12 hours and retroviral supernatants were harvested 24 hours after transfection. The retroviral vector supernatants then were tested (i) for binding affinity to collagen matrices using a modified ELISA (Hall, et al., *Human Gene Therapy,* Vol. 8, pgs. 2183–2192 (1997)) and (ii) for infectivity by the expression of β-galactosidase activity in NIH 3T3 cells. (Hall, et al., 1997).

In the ELISA assay, 50 ml of vector supernatant was applied to each collagen-coated microtiter well and allowed to bind for 20 minutes, followed by washing with 1×PBS, followed by incubation for 4 hours at room temperature at a primary antibody dilution of 1:1,000. A biotinylated goat antibody to rat IgG then was applied, followed by a streptavidin-horseradish peroxidase conjugate. Diaminobenzidine (DAB) was used as a chromogen followed by nickel chloride enhancement for microtiter plates.

Viral titers were determined and quantified based on expression of the β-galactosidase reporter gene. Briefly, $2.5\times10^4$ NIH 3T3 cells were plated in each well of 6 well plates prior to transduction. The medium was replaced with 1 ml of serial dilutions of viral supernatant with 8 mg/ml polybrene for 2 hours. One ml of fresh D10 was added to the cultures, which then were maintained overnight at 37° C. and 5% $CO_2$. The medium was replaced with fresh D10 and cultures were maintained for an additional 24 hours. Expression of β-galactosidase in the respective cultures was evaluated by X-gal staining 48 hours after transduction of the NIH 3T3 cells.

In another experiment, 1.5 ml of vector supernatant or buffer were incubated at 37° C. in 6-well plates in which an island of collagen was applied within a cloning ring, and washed twice with 1×PBS. Then, 1×10$^5$ NIH 3T3 cells, suspended in DMEM-10% FBS medium containing 8 mg/ml Polybrene, were plated into each well. The cultures were incubated at 37° C. overnight, replaced with D10 medium not containing polybrene, and stained with X-gal after an additional 24 hrs. at 37° C.

Figure 1:
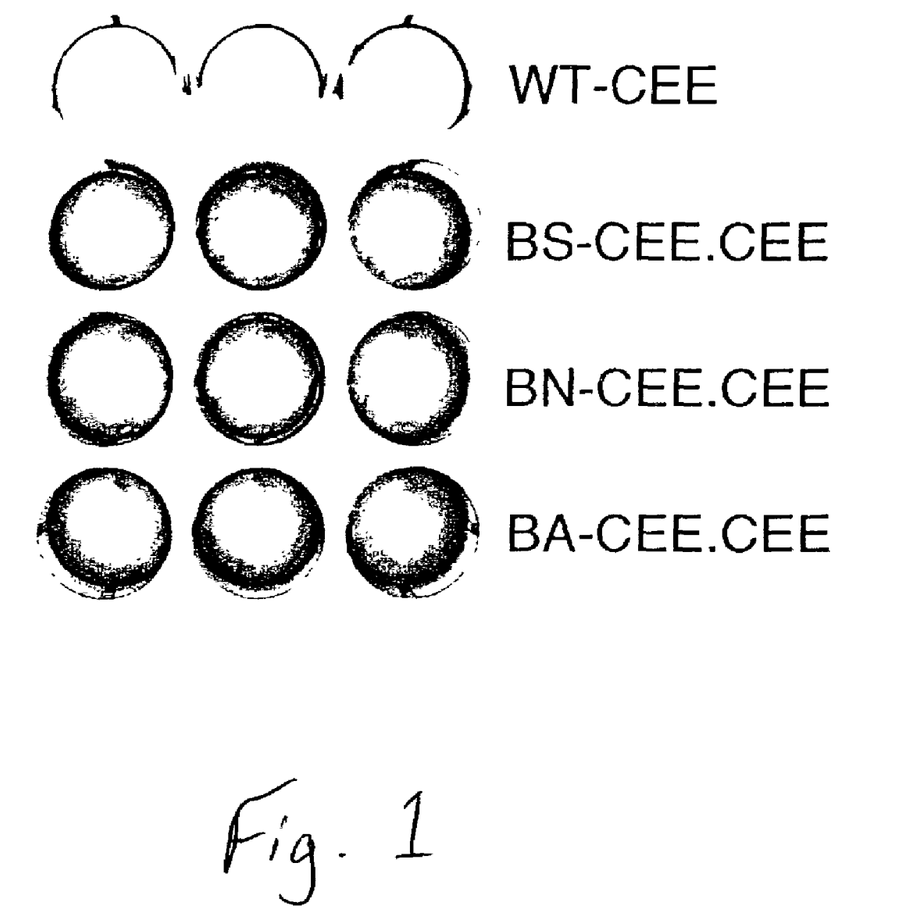

FIG. 1 shows ELISA results for the retroviral vectors WT-CEE, BS-CEE.CEE, BN-CEE.CEE, and BA-CEE.CEE. The vector WT-CEE is a wild-type vector with an ecotropic envelope protein. BS-CEE.CEE is a retroviral vector with a wild-type ecotropic envelope protein, and an "escort protein" envelope protein formed by inserting the collagen binding domain between BstEII and StuI sites of the CEE (ecotropic)-delta hinge construct. BN-CEE.CEE is a retroviral vector with a wild-type ecotropic envelope protein, and an "escort protein" envelope formed by inserting the collagen binding domain between the BstEII and NgoMI sites of the CEE (ecotropic)-delta hinge env construct. BA-CEE.CEE is a retroviral vector including a wild-type ecotropic envelope protein, and an "escort protein" envelope formed by inserting the collagen binding domain between the BstII and AvrII sites of the CEE (ecotropic)-delta hinge env construct.

As shown in FIG. 1, the BS-CEE.CEE, BN-CEE.CEE and BA-CEE.CEE vectors bound to the collagen-coated wells. Thus, it was determined that the majority of the receptor binding region of the envelope protein and a portion or all the hypervariable polyproline region could be removed and replaced with a collagen binding domain.

Example 2

Ig G Binding of Protein A-env Escort Proteins

A series of retroviral vectors including chimeric envelope proteins including Protein A (Lowenadler, et al., *Gene*, Vol. 58, pgs. 87–97 (1987)) which binds to Ig G, were constructed by employing (i) pHIT60; (ii) pHIT 112; (iii) plasmid encoding a chimeric envelope protein, wherein Protein A replaces a portion of the envelope or Protein A is inserted between amino acid residues of the envelope protein; and/or (iv) a plasmid encoding wild-type CEE or CAE envelope proteins. The plasmids are co-transfected into 293 T-cells as described in Example 1, followed by sodium butyrate treatment to produce high titer retroviral vectors. The following retroviral vectors were generated, as described in Table I below:

TABLE 1

| Vector | Construct |
| --- | --- |
| PABN | Protein A at BstEII and Ngo |
| PABN.CAE | Protein A at BstEII and Ngo + Wild Type CAE env |
| PABN.CEE | Protein A at BstEII and Ngo + Wild Type Cee env |
| PABA | Protein A at BstEII and Avr |
| PABA.CAE | Protein A at BstEII and Avr + Wild Type CAE env |
| PABA.CEE | Protein A at BstEII and Avr + Wild Type Cee env |
| PAP | Protein A at PstI (insert) |
| PAP.CAE | Protein A at PstI (insert) + Wild Type CAE env |
| PAP.CEE | Protein A at PstI (insert) + Wild Type CEE env |
| PAB | Protein A at BstEII (insert) |
| PAB.CAE | Protein A at BstEII (insert) + Wild type CAE env |
| PAB.CEE | Protein A at BstEII (insert) + Wild type Cee env |
| CAE | Wild Type CAE env |
| CEE | Wild type CEE env |
| CEE.C.PS | Wild type CEE + CAE Hinge at Pst Stu |

The binding affinity of the Protein A bearing virions for purified IgG was evaluated in comparison to wild type CEE and CAE virions using a modification of standard ELISA techniques described in Hall, 1997, except that the ELISA assay employed the 83A25 rat monoclonal antibody directed against the murine leukemia virus env protein (Evans, et al., *J. Virol.*, Vol. 64, No. 12, pgs. 6176–6183(1990)), and the wells were pre-coated with purified human Ig G (Gamma Immune N) instead of collagen Type I.

Figure 2:
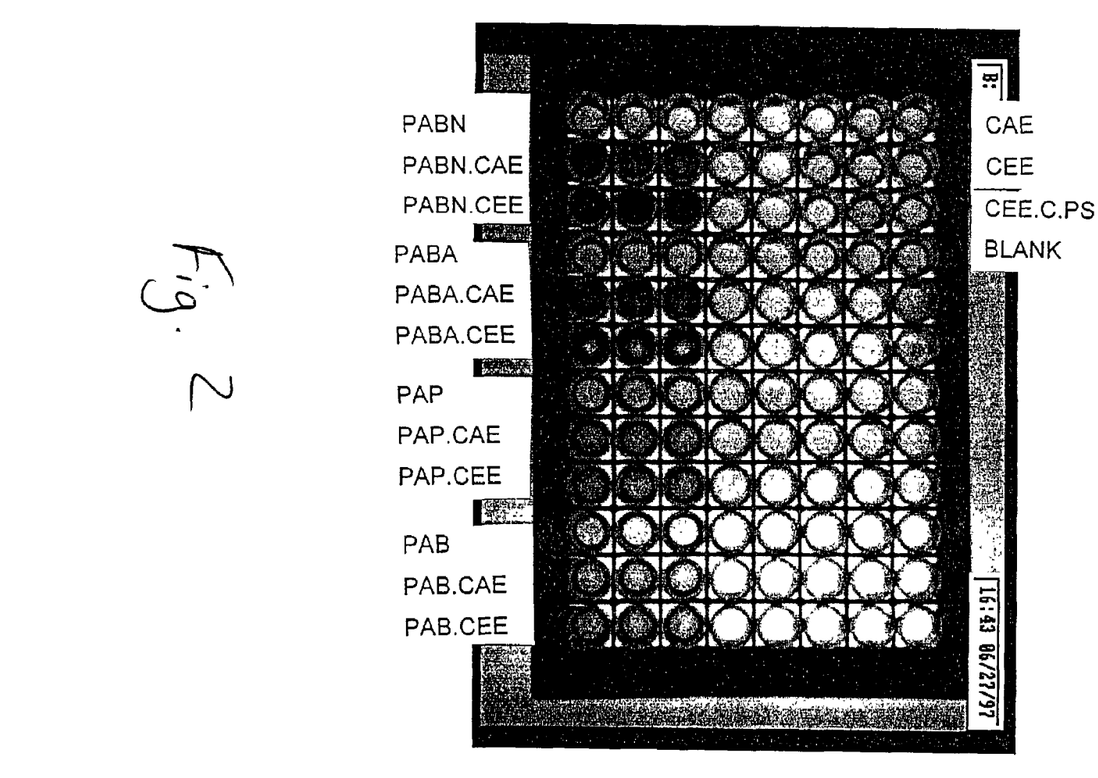

As shown in FIG. 2, the virions including a wild-type envelope protein, and an "escort protein" in which a portion of the envelope protein is removed and replaced with Protein A, remained bound to IgG (dark staining wells) upon washing with PBS, while the wild-type CEE and CAE virions were removed.

Example 3

Construction of Retroviral Vectors Having an Escort Protein Including Protein ZZ The retroviral vectors PABA.CAE and PABN.CAE were generated as described in Example 2. Vector PZBA.CAE is identical to PABA.CAE, except that in the "escort protein," protein ZZ (Nilsson, et al., *Protein Eng.*, VOl. 1, pgs. 107–113 (1987)), a 116 amino acid residue protein which binds to IgG, was inserted between the BstEII and AvrII sites. The vectors had viral titers approaching those of wild-type envelopes (PABA.CAE=2×10$^6$ cfu/ml; PZBA.CAE=2×10$^6$ cfu/ml; PABN.CAE=1×10$^6$ cfu/ml; wild-type CAE=2×10$^6$ cfu/ml), and demonstrated high affinity binding to IgG1 coated ELISA plates. The ELISA assay was conducted in accordance with the procedure described in Example 2.

Wells containing 5×10$^5$ KSY1 Kaposi sarcoma cells (Masood, et al., *Proc. Nat Acad. Sci.*, Vol. 94, pgs. 979–984 (1994)) were contacted with 1,000 ng or 5,000 ng of KDR/Flk-1 antibody, or with Polybrene. One well was contacted with neither material. The cells which were contacted with antibody then were contacted with PABA.CAE or wild-type CAE having a titer of 2×10$^6$ cfu/ml at a multiplicity of infection (MOI) of 4. The cells then were stained with X-gal, and blue colonies were counted. The results are given in Table 2 below.

TABLE 2

| KSY1 Sample 5 × 10$^5$ cells/well | KDR/Flk-1 Ab ng | Vector 2 × 10$^6$ cfu/ml | # Blue Colonies MOI = 4 |
| --- | --- | --- | --- |
| 1 | 1000 | PABA.CAE | 648 |
| 2 | 5000 | PABA.CAE | 946 |
| 3 | 5000 | WT.CAE | 66 |
| 4 | 0 | None | 0 |
| 5 | Polybrene | None | 0 |

In another experiment, wells containing 1×10$^5$ KSY1 cells in each well were contacted with 0 ng, 1,000 ng. or 5,000 ng of KDR/Flk-1 antibody. The cells that were contacted with antibody then were contacted with PABN.CAE or wild-type CAE having a titer of 1×10$^6$ cfu/ml, and at a multiplicity of infection (MOI) of 10. The cells then were stained with X-gal and the number of blue colonies were counted. The results are given in Table 3 below.

TABLE 3

| KSY1 Sample 1 × 10⁵ cells/well | KDR/Flk-1 Ab ng | Vector 1 × 10⁶ cfu/ml | # Blue Colonies MOI = 10 |
|---|---|---|---|
| 1 | 1000 | PABN.CAE | 1560 |
| 2 | 5000 | PABN.CAE | 2554 |
| 3 | 5000 | WT.CAE | 20 |
| 4 | 0 | None | 0 |
| 5 | 0 | Polybrene | 0 |

The above results indicate that the vectors including the "escort proteins" exhibited an antibody-dependent and dose-dependent increase in efficiency of transduction of KDR/Flk-1 antibody-coated endothelial KSY1 Kaposi's sarcoma cells, when compared to vectors including only a wild-type env. The data indicate that transduction efficiency is enhanced by molecular "tethering" of chimeric virions against the endothelial cell surface. Based upon the above results, such IgG-targeted vectors may provide an efficient gene delivery vehicle for delivering genes to endothelial cell receptors in transplanted vascular grafts and organs, including hearts, kidneys, lungs, pancreases, and livers.

The disclosures of all patents, publications (including published patent applications), database accession numbers, and depository accession numbers referenced in this specification are spec -continued <210> SEQ ID NO 2
<211> LENGTH: 60
<212> TYPE: PRT
<213> ORGANISM: Moloney murine leukemia virus

<400> SEQUENCE: 2

Gly Pro Arg Val Pro Ile Gly Pro Asn Pro Val Leu Pro Asp Gln Arg
1               5                   10                  15

Leu Pro Ser Ser Pro Ile Glu Ile Val Pro Ala Pro Gln Pro Pro Ser
            20                  25                  30

Pro Leu Asn Thr Ser Tyr Pro Pro Ser Thr Thr Ser Thr Pro Ser Thr
        35                  40                  45

Ser Pro Thr Ser Pro Ser Val Pro Gln Pro Pro
    50                  55                  60

<210> SEQ ID NO 3
<211> LENGTH: 687
<212> TYPE: DNA
<213> ORGANISM: Moloney murine leukemia virus

<400> SEQUENCE: 3
gcttcgcccg gctccagtcc tcatcaagtc tataatatca cctgggaggt aaccaatgga      60
gatcgggaga cggtatgggc aacttctggc aaccaccctc tgtggacctg gtggcctgac     120
cttaccccag atttatgtat gttagcccac catggaccat cttattgggg ctagaaatat     180 caatccccctt tttcttctcc cccggggccc ccttgttgct caggggcag cagcccaggc     240 tgttccagag actgcgaaga acctttaacc tccctcaccc ctcggtgcaa cactgcctgg     300
aacagactca agctagacca gacaactcat aaatcaaatg agggatttta tgtttgcccc     360
gggccccacc gcccccgaga atccaagtca tgtgggggtc cagactcctt ctactgtgcc     420
tattggggct gtgagacaac cggtagagct tactggaagc cctcctcatc atgggatttc     480
atcacagtaa acaacaatct cacctctgac caggctgtcc aggtatgcaa agataataag     540
tggtgcaacc ccttagttat tcggtttaca gacgccggga gacgggttac ttcctggacc     600
acaggacatt actggggctt acgtttgtat gtctccggac aagatccagg cttacatttt    660
gggatccgac tcagatacca aaatcta                                          687

<210> SEQ ID NO 4
<211> LENGTH: 180
<212> TYPE: DNA
<213> ORGANISM: Moloney murine leukemia virus

<400> SEQUENCE: 4
ggaccccgag tccccatagg gcccaaccca gtattacccg accaaagact cccttcctca      60
ccaatagaga ttgtaccggc tccacagcca cctagccccc tcaataccag ttaccccct     120 tccactacca gtacaccctc aacctcccct acaagtccaa gtgtcccaca gccacccca     180

<210> SEQ ID NO 5
<211> LENGTH: 16
<212> TYPE: PRT
<213> ORGANISM: Homo sapiens

<400> SEQUENCE: 5

Cys Gln Ala Gly Thr Phe Ala Leu Arg Gly Asp Asn Pro Gln Gly Cys
1               5                   10                  15

```
<210> SEQ ID NO 6
<211> LENGTH: 15
<212> TYPE: PRT
<213> ORGANISM: Unknown
<220> FEATURE:
<223> OTHER INFORMATION: Polypeptide which binds to the integrin avB3
      found on melanoma cells

<400> SEQUENCE: 6

Gly Glu Arg Gly Asp Gly Ser Phe Phe Ala Phe Arg Ser Pro Phe
1               5                   10                  15

<210> SEQ ID NO 7
<211> LENGTH: 10
<212> TYPE: PRT
<213> ORGANISM: Unknown
<220> FEATURE:
<223> OTHER INFORMATION: polypeptide binding region that binds to
      collagen

<400> SEQUENCE: 7

Trp Arg Glu Pro Ser Phe Met Ala Leu Ser
1               5                   10

<210> SEQ ID NO 8
<211> LENGTH: 6
<212> TYPE: PRT
<213> ORGANISM: Unknown
<220> FEATURE:
<223> OTHER INFORMATION: polypeptide which binds fibronectin

<400> SEQUENCE: 8

Gly Gly Trp Ser His Trp
1               5

<210> SEQ ID NO 9
<211> LENGTH: 16
<212> TYPE: PRT
<213> ORGANISM: Unknown
<220> FEATURE:
<223> OTHER INFORMATION: polypeptide shown in Example 1 including the
      collagen binding domain and linkers.

<400> SEQUENCE: 9

Gly His Met Trp Arg Glu Pro Ser Phe Met Ala Leu Ser Gly Ala Ser
1               5                   10                  15

<210> SEQ ID NO 10
<211> LENGTH: 55
<212> TYPE: DNA
<213> ORGANISM: artificial sequence
<220> FEATURE:
<223> OTHER INFORMATION: deoxyoligonucleotide

<400> SEQUENCE: 10
taaccggcca tatgtggcgc gaaccgagct tcatgctctg agcggtgcta gcaac         55

<210> SEQ ID NO 11
<211> LENGTH: 55
<212> TYPE: DNA
<213> ORGANISM: artificial sequence
<220> FEATURE:
<223> OTHER INFORMATION: deoxyoligonucleotide

<400> SEQUENCE: 11
gccggtatac accgcgcttg gctcgaagta cgagactcgc cacgatcgtt ggatc         55
```

```
<210> SEQ ID NO 12
<211> LENGTH: 55
<212> TYPE: DNA
<213> ORGANISM: artificial sequence
<220> FEATURE:
<223> OTHER INFORMATION: deoxyoligonucleotide

<400> SEQUENCE: 12
gtaaccggcc atatgtggcg cgaaccgagc ttcatggctc tgagcggtgc tagcg        55

<210> SEQ ID NO 13
<211> LENGTH: 55
<212> TYPE: DNA
<213> ORGANISM: artificial sequence
<220> FEATURE:
<223> OTHER INFORMATION: deoxyoligonucleotide

<400> SEQUENCE: 13
gccggtatac accgcgcttg gctcgaaagt accgagactc gccacgatcg cggcc        55

<210> SEQ ID NO 14
<211> LENGTH: 59
<212> TYPE: DNA
<213> ORGANISM: artificial sequence
<220> FEATURE:
<223> OTHER INFORMATION: deoxyoligonucleotide

<400> SEQUENCE: 14
gtaaccggcc atatgtggcg cgaaccgagc ttcatggctc tgagcggtgc tagctcagg    59

<210> SEQ ID NO 15
<211> LENGTH: 54
<212> TYPE: DNA
<213> ORGANISM: artificial sequence
<220> FEATURE:
<223> OTHER INFORMATION: deoxyoligonucleotide

<400> SEQUENCE: 15
gccggtatac accgcgcttg gctcgaagta ccgagactcg ccacgatcga gtcc         54
```

What is claimed is:

1. A modified retroviral envelope protein, wherein prior to modification, the retroviral envelope protein included a surface protein comprising: (i) a receptor binding region having the sequence of SEQ ID NO: 1; (ii) a hypervariable polyproline region having the sequence of SEQ ID NO: 2; and (iii) a C-terminus of said surface protein, wherein said modified retroviral envelope protein has been modified such that at least 90% of the amino acid residues of the receptor binding region and residues 1 through 35 of SEQ ID NO: 2 have been removed and replaced with a non-retroviral protein or peptide.

2. The protein of claim 1 wherein, in said modified retroviral envelope protein, amino acid residues 19 through 229 of SEQ ID NO: 1 have been removed.

* * * * *